(12) United States Patent
Lennox

(10) Patent No.: US 7,008,445 B2
(45) Date of Patent: Mar. 7, 2006

(54) METHOD AND DEVICE FOR RAPIDLY INDUCING HYPOTHERMIA

(75) Inventor: Charles D. Lennox, Hudson, NH (US)

(73) Assignee: MedCool, Inc., Wellesley, MA (US)

( * ) Notice: Subject to any disclaimer, the term of this patent is extended or adjusted under 35 U.S.C. 154(b) by 11 days.

(21) Appl. No.: 10/424,391

(22) Filed: Apr. 25, 2003

(65) Prior Publication Data

US 2003/0236561 A1    Dec. 25, 2003

Related U.S. Application Data

(60) Provisional application No. 60/376,249, filed on Apr. 29, 2002.

(51) Int. Cl.
*A61F 7/00* (2006.01)
(52) U.S. Cl. .................. 607/109; 128/898; 607/104
(58) Field of Classification Search ............ 128/898; 607/108–110
See application file for complete search history.

(56) References Cited

U.S. PATENT DOCUMENTS

| | | | |
|---|---|---|---|
| 26,663 A | 1/1860 | French | |
| 998,804 A | 7/1911 | Salisbury | |
| 2,043,721 A | 6/1936 | Warwick | 34/26 |
| 2,224,876 A | 12/1940 | Matys | 34/26 |
| 2,255,751 A | 9/1941 | Bancel | 128/144 |
| 2,272,481 A | 2/1942 | Rinkes et al. | 128/66 |
| 2,416,788 A | 3/1947 | Andrews | 34/99 |
| 2,512,990 A | 6/1950 | Akerman | 2/81 |
| 2,540,547 A | 2/1951 | Rodert | 2/81 |
| 2,566,600 A | 9/1951 | Colon | 128/65 |
| 2,706,988 A | 4/1955 | Weber | 128/402 |
| 3,085,405 A | 4/1963 | Frantti | 62/3 |
| 3,153,720 A | 10/1964 | Petronio et al. | 219/211 |
| 3,229,681 A | 1/1966 | Gluckstein | 126/204 |
| 3,348,236 A | 10/1967 | Copeland | 2/2 |
| 3,378,004 A | 4/1968 | Claycomb et al. | 128/66 |
| 3,449,761 A | 6/1969 | Long | 2/2.1 |
| 3,477,424 A | 11/1969 | Tracy | 128/66 |

(Continued)

FOREIGN PATENT DOCUMENTS

JP      05220186 A      8/1993

(Continued)

OTHER PUBLICATIONS

International Search Report from International Application No. PCT/US03/35930, filed Nov. 12, 2003, 2 pages.

(Continued)

*Primary Examiner*—Henry M Johnson, III
(74) *Attorney, Agent, or Firm*—Thomas J. Engellenner; Jeffrey J. Duquette; Nutter McClennen & Fish LLP

(57) ABSTRACT

Disclosed is a system and method for inducing therapeutic levels of hypothermia in a patient in the emergent care setting. The system consists of a small battery operated console and one or more garments. The garments are connected to the console by one or more umbilicals. The console provides cold fluid to the garments under pressure and the garment cools the surface of the body. Fluid returns from the garment back to the console in a closed loop fashion. The console contains an electrical battery and a thermal battery that provides operation of the system for more than one hour. The cooling capacity of the system is sufficient to induce therapeutic levels of hypothermia in approximately 30 to 90 minutes in most patients. Use of the system does not preclude any therapeutic or diagnostic interventions that are commonly performed in the emergent care setting.

39 Claims, 8 Drawing Sheets

U.S. PATENT DOCUMENTS

| | | | | |
|---|---|---|---|---|
| 3,587,577 A | * | 6/1971 | Smirnov | 604/23 |
| 3,610,323 A | | 10/1971 | Troyer | 165/46 |
| 3,648,289 A | | 3/1972 | Moreland | 2/2.1 R |
| 3,738,367 A | | 6/1973 | Hardy | 128/379 |
| 3,786,809 A | | 1/1974 | Kitrilakis | 128/191 |
| 3,839,621 A | | 10/1974 | Hariu | 219/211 |
| 3,892,225 A | | 7/1975 | Twose | 126/204 |
| 3,905,367 A | | 9/1975 | Dapcich | 128/254 |
| 3,908,655 A | | 9/1975 | Lund | 128/256 |
| 4,067,064 A | | 1/1978 | Cerniway et al. | 2/2.1 R |
| 4,074,369 A | | 2/1978 | Harmon | 4/159 |
| 4,108,146 A | | 8/1978 | Golden | 128/400 |
| 4,114,620 A | | 9/1978 | Moore et al. | 128/254 |
| 4,139,004 A | | 2/1979 | Gonzalez, Jr. | 128/82.1 |
| 4,149,541 A | | 4/1979 | Gammons et al. | 128/400 |
| 4,167,932 A | | 9/1979 | Zebuhr | 126/208 |
| 4,172,495 A | | 10/1979 | Zebuhr et al. | 165/46 |
| 4,194,247 A | | 3/1980 | Melander | 2/2 |
| 4,224,941 A | | 9/1980 | Stivala | 128/207.26 |
| 4,237,877 A | | 12/1980 | Boehler | 128/204.15 |
| 4,286,439 A | | 9/1981 | Pasternack | 62/259.3 |
| 4,294,225 A | | 10/1981 | Mayo | 126/204 |
| 4,353,359 A | | 10/1982 | Milbauer | 128/66 |
| 4,390,997 A | | 7/1983 | Hinz et al. | 2/81 |
| 4,398,535 A | | 8/1983 | Guibert | 128/399 |
| 4,418,745 A | | 12/1983 | Roehr | 165/46 |
| 4,425,916 A | | 1/1984 | Bowen | 128/403 |
| 4,523,594 A | | 6/1985 | Kuznetz | 128/402 |
| 4,566,455 A | | 1/1986 | Kramer | 128/380 |
| 4,572,188 A | | 2/1986 | Augustine et al. | 128/380 |
| 4,575,097 A | | 3/1986 | Brannigan et al. | 128/402 |
| 4,691,762 A | | 9/1987 | Elkins et al. | 165/46 |
| 4,738,119 A | | 4/1988 | Zafred | 62/259.3 |
| 4,747,408 A | | 5/1988 | Chuan-Chih | 128/400 |
| 4,753,242 A | | 6/1988 | Saggers | 128/380 |
| 4,770,169 A | * | 9/1988 | Schmoegner et al. | 128/207 |
| 4,781,193 A | | 11/1988 | Pagden | 128/402 |
| 4,844,072 A | | 7/1989 | French et al. | 128/400 |
| 4,869,250 A | | 9/1989 | Bitterly | 128/400 |
| 4,886,063 A | | 12/1989 | Crews | 128/403 |
| 4,920,963 A | | 5/1990 | Brader | 128/402 |
| 4,969,880 A | | 11/1990 | Zamierowski | 604/305 |
| 4,987,618 A | | 1/1991 | Tolbert | 4/515 |
| 4,998,415 A | | 3/1991 | Larsen | 62/231 |
| 5,062,424 A | | 11/1991 | Hooker | 128/379 |
| 5,097,829 A | | 3/1992 | Quisenberry | 128/400 |
| 5,100,261 A | | 3/1992 | Plemon | 405/186 |
| 5,167,227 A | | 12/1992 | Meserlian | 128/64 |
| 5,168,576 A | | 12/1992 | Krent et al. | 2/2 |
| 5,174,285 A | | 12/1992 | Fontenot | 128/400 |
| 5,230,335 A | | 7/1993 | Johnson, Jr. et al. | 128/400 |
| 5,235,709 A | | 8/1993 | Terlep | 4/515 |
| 5,241,951 A | | 9/1993 | Mason et al. | 607/104 |
| 5,269,369 A | | 12/1993 | Faghri | 607/104 |
| 5,292,347 A | * | 3/1994 | Pompei | 607/104 |
| 5,300,105 A | | 4/1994 | Owens | 607/104 |
| D347,491 S | | 5/1994 | Holloway | D28/20 |
| 5,314,455 A | | 5/1994 | Johnson, Jr. et al. | 607/104 |
| 5,330,519 A | | 7/1994 | Mason et al. | 607/104 |
| 5,342,411 A | | 8/1994 | Maxted et al. | 607/107 |
| 5,383,918 A | | 1/1995 | Panetta | 607/104 |
| 5,383,919 A | | 1/1995 | Kelly et al. | 607/104 |
| 5,411,493 A | | 5/1995 | Rodriguez | 604/290 |
| 5,417,720 A | | 5/1995 | Mason | 607/104 |
| 5,423,087 A | | 6/1995 | Krent et al. | 2/2 |
| 5,429,534 A | | 7/1995 | Cano | 440/88 |
| 5,438,707 A | | 8/1995 | Horn | 2/69 |
| 5,456,701 A | | 10/1995 | Stout | 607/104 |
| 5,470,353 A | | 11/1995 | Jensen | 607/104 |
| 5,486,206 A | | 1/1996 | Avery | 607/104 |
| 5,486,207 A | * | 1/1996 | Mahawili | 607/104 |
| 5,496,357 A | | 3/1996 | Jensen et al. | 607/108 |
| 5,507,792 A | | 4/1996 | Mason et al. | 607/104 |
| 5,533,354 A | | 7/1996 | Pirkle | 62/259.3 |
| 5,562,604 A | | 10/1996 | Yablon et al. | 601/148 |
| 5,603,728 A | | 2/1997 | Pachys | 607/110 |
| 5,609,619 A | | 3/1997 | Pompei | 607/104 |
| 5,634,890 A | | 6/1997 | Morris | 601/166 |
| 5,643,336 A | | 7/1997 | Lopez-Claros | 607/104 |
| 5,683,438 A | | 11/1997 | Grahn | 607/104 |
| 5,697,920 A | * | 12/1997 | Gibbons | 604/289 |
| 5,792,216 A | | 8/1998 | Kappel | 607/107 |
| 5,800,483 A | | 9/1998 | Vought | 607/104 |
| 5,871,526 A | | 2/1999 | Gibbs et al. | 607/104 |
| 5,913,885 A | | 6/1999 | Klatz et al. | 607/104 |
| 5,947,914 A | | 9/1999 | Augustine | 602/2 |
| 5,954,680 A | | 9/1999 | Augustine | 602/42 |
| 5,960,469 A | | 10/1999 | Nuckols et al. | 2/2.1 |
| 5,964,721 A | | 10/1999 | Augustine | 602/2 |
| 5,964,723 A | | 10/1999 | Augustine | 602/42 |
| 5,976,176 A | | 11/1999 | Webb, II | 607/104 |
| 5,986,163 A | | 11/1999 | Augustine | 602/42 |
| 6,030,412 A | | 2/2000 | Klatz et al. | 607/104 |
| 6,045,518 A | | 4/2000 | Augustine | 602/2 |
| 6,050,099 A | | 4/2000 | Lopa et al. | 62/259.3 |
| 6,086,609 A | | 7/2000 | Buckley | 607/104 |
| 6,109,338 A | | 8/2000 | Butzer | 165/46 |
| 6,113,561 A | | 9/2000 | Augustine | 602/2 |
| 6,113,626 A | | 9/2000 | Clifton et al. | 607/96 |
| 6,117,164 A | | 9/2000 | Gildersleeve et al. | 607/108 |
| 6,128,784 A | | 10/2000 | Frank | 2/102 |
| 6,149,674 A | | 11/2000 | Borders | 607/96 |
| 6,156,059 A | * | 12/2000 | Olofsson | 607/109 |
| 6,178,562 B1 | | 1/2001 | Elkins | 2/458 |
| 6,197,045 B1 | | 3/2001 | Carson | 607/104 |
| 6,210,427 B1 | | 4/2001 | Augustine et al. | 607/97 |
| 6,213,966 B1 | | 4/2001 | Augustine | 602/2 |
| 6,217,535 B1 | | 4/2001 | Augustine | 602/2 |
| 6,230,501 B1 | | 5/2001 | Bailey, Sr. et al. | 62/51.1 |
| 6,238,427 B1 | | 5/2001 | Matta | 607/104 |
| 6,241,697 B1 | | 6/2001 | Augustine | 602/2 |
| 6,241,698 B1 | | 6/2001 | Augustine | 602/2 |
| 6,241,756 B1 | | 6/2001 | Kappel | 607/107 |
| 6,245,094 B1 | | 6/2001 | Pompei | 607/104 |
| 6,245,096 B1 | | 6/2001 | Tomic-Edgar et al. | 607/107 |
| 6,264,622 B1 | | 7/2001 | Augustine | 602/2 |
| 6,276,155 B1 | | 8/2001 | Siman-Tov et al. | 62/259.3 |
| 6,277,143 B1 | | 8/2001 | Klatz et al. | 607/104 |
| 6,312,453 B1 | | 11/2001 | Stefanile et al. | 607/109 |
| 6,349,412 B1 | | 2/2002 | Dean | 2/102 |
| 6,352,550 B1 | | 3/2002 | Gildersleeve et al. | 607/108 |
| 6,371,976 B1 | | 4/2002 | Vrzalik et al. | 607/104 |
| 6,375,673 B1 | | 4/2002 | Clifton et al. | 607/104 |
| 6,375,674 B1 | | 4/2002 | Carson | 607/104 |
| 6,406,447 B1 | * | 6/2002 | Thrash et al. | 601/160 |
| 6,406,448 B1 | | 6/2002 | Augustine | 602/2 |
| 6,407,307 B1 | | 6/2002 | Augustine | 602/42 |
| 6,419,651 B1 | | 7/2002 | Augustine | 602/2 |
| 6,419,691 B1 | | 7/2002 | Hanner | 607/108 |
| 6,423,018 B1 | | 7/2002 | Augustine | 602/2 |
| 6,461,379 B1 | | 10/2002 | Carson et al. | 607/104 |
| 6,500,200 B1 | | 12/2002 | Kushnir | 607/104 |
| 6,520,982 B1 | | 2/2003 | Boynton et al. | 607/104 |
| 6,551,347 B1 | | 4/2003 | Elkins | 607/104 |
| 6,581,400 B1 | | 6/2003 | Augustine et al. | 62/259.3 |
| 6,605,051 B1 | | 8/2003 | Augustine | 602/2 |
| 2002/0103520 A1 | | 8/2002 | Latham | 607/108 |
| 2002/0161419 A1 | | 10/2002 | Carson et al. | 607/104 |
| 2003/0163183 A1 | | 8/2003 | Carson | 607/108 |

FOREIGN PATENT DOCUMENTS

| | | | |
|---|---|---|---|
| JP | 05220187 A | 8/1993 | |

OTHER PUBLICATIONS

Tooley, et al., "Head Cooling with Mild Systemic Hypothermia in Anesthetized Piglets in Neuroprotective", Annals of Neurology, vol. 53, No. 1, pp. 65-72, Jan. 2003.

Tooley, et al., "Significant Selective Head Cooling can be Maintained Long-Term After Global Hypoxia Ischemia in Newborn Piglets", Pediatrics, vol. 109, No. 4, pp. 643-649, Apr. 2002.

Hachimi-Idrissi, et al., "Mild Hypothermia Induced by a Helmet Device: A Clinical Feasibility Study", Resuscitation 51:275-281 (2001).

* cited by examiner

METHOD AND DEVICE FOR RAPIDLY INDUCING HYPOTHERMIA

CROSS REFERENCE TO RELATED APPLICATIONS

This application is entitled to the benefit of Provisional Patent Application Ser. No. 60/376,249 filed Apr. 29, 2002.

BACKGROUND

1. Field of Invention

This invention relates to a method, device, and system for rapidly inducing protective levels of hypothermia in the brain and the body.

2. Description of Prior Art

Patients suffering from stroke, cardiac arrest, or head trauma, or have undergone invasive brain or vascular surgery are at risk from secondary ischemic brain injury. Secondary ischemic brain injury is a result of the innate healing response of the brain to the original insult caused by several not completely understood mechanisms. Regardless of the specific mechanisms involved, the end result is swelling of the brain caused by edema, which can lead to a critical or terminal rise in intra-cranial pressure, or cell death and loss of brain function.

Patients suffering heart attack often suffer damage to their heart due to secondary injury caused by ischemia. Ischemic damage to the heart is the main cause of death and disability following heart attack.

It has long been known that hypothermia is neuroprotective. Hypothermia has a positive affect on all know mechanisms that lead to secondary brain injury. Hypothermia is routinely used during brain and other invasive surgeries to protect the brain from surgical interruptions in blood flow. Hypothermia has also been shown to be effective in controlling swelling of the brain in trauma and stroke patients.

It has been more recently discovered the hypothermia is effective at protecting the heart from secondary ischemic injury due to heart attack.

The effectiveness of hypothermia is a function of depth, duration, and the amount of time that elapses between the original insult and achievement of protective levels of hypothermia; the earlier, deeper (within a range of 30° C. and 35° C.), and/or the longer hypothermia is applied the more protective it is. However, hypothermia has historically been applied systemically, and the depth and duration of hypothermia is limited by the patient's ability to tolerate the therapy.

Systemic hypothermia has historically been accomplished by immersion of the patient's body in a cool bath. Today there are several commercial systemic hypothermia systems available. They consist of blankets or pads where cooled water is circulated through channels in the walls of the blanket or pad, and the patient's body is maintained in intimate contact. Medivan Corp. manufactures an example of a modem hypothermia system under the trade name Arctic Sun Cooling System.

Systemic hypothermia has been demonstrated to be effective in reducing secondary injury from stroke, trauma, and surgery however, there are several drawbacks to this approach: 1) It may take several hours to lower a patient's body to therapeutic temperatures. This delay in achieving therapeutic temperatures allows for the progression of irreversible secondary injury to the brain and heart. 2) Hypothermia cannot be initiated until after the patient has been admitted to the hospital. 3) The entire patient's body is cooled in a slow and uniform manner; protective levels of hypothermia in the brain is not achieved until the whole body reaches protective levels of hypothermia.

Attempts have been made to induce hypothermia by cooling the surface of the head. A company, Flexoversal from Hiden, Germany manufactures a head cooling device under the trade name of "Hypotherm Gel Cap" This device is a head cap with a gel substance within its walls. The "Gel Cap" is placed into a freezer prior to use, then is fitted to the head of a patient. The gel within the walls of the cap absorbs heat from the head. Also, described in the art are cooling caps that have cold fluid circulating through the walls of the cap to absorb heat from the head. Reports from clinical trials using such devices have been disappointing in that they have not been effective in inducing hypothermia in patients. Although, theoretically these devises should be capable in inducing hypothermia, there are several practical limitations in design of the devices, and in the way they are used that limits effectiveness. A significant problem is that hair; especially dry hair is a very effective insulator. There is significant variation from patient to patient in the thickness of hair on the head, and its distribution. A device that does not address the insulating effect of hair, and its variability among patients is will ineffective in inducing hypothermia in a consistent manner. A second significant problem with head cooling described in the art is that the cooling medium (gel, or circulating water) is separated from the head by the material that the device is made of Most devices described in the art are made of plastic or woven material, both of which are highly insulative and greatly reduce the amount of heat that is transferred from the head into the cooling medium.

Nowhere in the art is it suggested that directing evenly distributed jets of saline at near 0° C. at the scalp in a vigorous manner will effectively and consistently induce hypothermia regardless of the amount of hair on the head, or its distribution on the head. Nowhere described in the art is a means of directing evenly distributed jets of saline at the scalp and a means of scavenging the saline for reuse in a closed loop system. Nowhere described in the art is a system consisting of: a small portable console, and a head cooling device, where the head cooling device is connected to the console by an umbilical, where the head cooling device and console work in a continuous operational relationship with each other to direct jets of saline at near 0° C. in an evenly distributed manner at the scalp, to then scavenge the expended saline from the vicinity of the head and return the expended saline to the console where the saline is then cooled to near 0° C. and where the saline is then returned to the head cooling device where it is once again directed at the scalp.

SUMMARY

Therefore, it is an object of this invention to provide a method and apparatus for preventing secondary ischemic injury in patients with an ischemic condition by inducing hypothermia. In accordance with one aspect of this invention, hypothermia is induced by placing a cooling device on the head of a patient, then cooling the head of the patient thereby cooling the body of the patient. In accordance with another aspect of this invention, apparatus for inducing hypothermia is provided that is portable, and may used by emergency medical personnel in the pre-hospital setting. In accordance with another aspect of this invention, a method and apparatus is provided that induces hypothermia such that the brain is cooled first and to a greater degree than the rest of the body. In accordance with another aspect of this invention, a method and apparatus is provided that effectively cools the head, and thereby cools the body, where the effectiveness the head cooling is unaffected by the thickness of the patient's hair or its distribution on the head. In accordance with another aspect of this invention, apparatus for inducing hypothermia includes a head-cooling device, and a portable console, where the head-cooling device and the console are connected by an umbilical. In accordance with another aspect of this invention, apparatus for inducing hypothermia includes a head-cooling device and a portable console where the head-cooling device and the console work in operational relationship to direct evenly distributed jets of cooling fluid at the scalp of a patient to cool the scalp, thereby cooling the body of the patient. In accordance with another aspect of this invention, apparatus for inducing hypothermia includes a head-cooling device and a portable console where the head-cooling device and the console work in a closed loop operational relationship where the console provides a means of providing cooling fluid to the head-cooling device under pressure, and where the head-cooling device directs evenly distributed jets of cooling fluid at the scalp of the patient, and where the head-cooling device and the console provide a means to scavenge the cooling fluid from the head-cooling device and return the scavenged cooling fluid to the console. In accordance with another aspect of this invention, apparatus for inducing hypothermia includes a head-cooling device and a portable console, where the console contains a rechargeable electrical battery and a rechargeable thermal battery, where the electrical battery provides energy to the electrical components within the console, and the thermal battery provides a means to remove heat from the cooling fluid, and therefore the patients body. In accordance with another aspect of this invention, apparatus for inducing hypothermia includes a head-cooling device and a portable console, where the console, in conjunction with the head-cooling device provides cooling for a period of time based on the electrical energy stored in the electrical battery, and the thermal absorbsion capacity stored in the thermal battery. In accordance with another aspect of this invention, apparatus for inducing hypothermia includes a head-cooling device and a portable console, where the console contains a cooling fluid reservoir and a thermal battery, where the cooling fluid reservoir, and the thermal battery are modular, and may be quickly removed from the console and replaced. In accordance with another aspect of this invention, apparatus for inducing hypothermia includes a head-cooling device, a neck-cooling device, and a portable console, where the head-cooling device and the neck-cooling device are connected to the console by a common umbilical, or by separate umbilicals. In accordance with another aspect of this invention, apparatus for inducing hypothermia includes a head-cooling device, a neck-cooling device, and a portable console, where the head-cooling device is a cap or a helmet that is fitted to the patient's head, and where the neck-cooling device is a collar that is fitted to the patients neck. In accordance with another aspect of this invention, apparatus for inducing hypothermia includes a head-cooling device, a neck-cooling device and a portable console, where the neck-cooling device is a collar which contains fluid channels within its walls, and where the console provides a means to circulate cooling fluid through said fluid channels to provide neck cooling. In accordance with another aspect of this invention, apparatus for inducing hypothermia includes a head-cooling device, a neck-cooling device, and a portable console, where the head-cooling device may be used in conjunction with the neck-cooling device, or without the neck-cooling device. In accordance with another aspect of this invention, apparatus for inducing hypothermia includes a head-cooling device, a neck-cooling device and a portable console, where the head-cooling device consists of a cap which contains fluid channels within the wall of the cap, and where the console provides a means to circulate cooling fluid through said fluid channels in the cap to provide head cooling. In accordance with another aspect of this invention, a method of preventing secondary ischemic injury in a patient with an ischemic condition is provided where evenly distributed jets of cooling fluid is directed at the scalp of a patient. In accordance with another aspect of this invention, a method of preventing secondary ischemic injury in a patient with an ischemic condition is provided where evenly distributed jets of cooling fluid is directed at the scalp of the patient using a head-cooling device and the neck of the patient is cooled using a neck-cooling device. In accordance with another aspect of this invention, a method of preventing secondary ischemic injury in a patient with an ischemic condition is provided where evenly distributed jets of cooling fluid is directed at the scalp of the patient using a head-cooling device, and the neck of the patient is cooled using a neck-cooling device, where the means of cooling the head and the neck is provided by a portable console. In accordance with another aspect of this invention, a method of preventing secondary ischemic injury in a patient with an ischemic condition is provided where evenly distributed jets of cooling fluid is directed at the scalp of the patient using a head-cooling device, and the neck of the patient is cooled using a neck-cooling device, where the means of cooling the head and the neck is provided by a console where the console is provided electrical energy from a wall outlet, and cooling is provided by a refrigeration unit. In accordance with another aspect of this invention, apparatus for preventing secondary ischemic injury in a patient with an ischemic condition is provided where evenly distributed jets of cooling fluid is directed at the scalp of the patient using a head-cooling device, and the neck of the patient is cooled using a neck-cooling device, where the means of cooling the head and the neck is provided by a console where the console is provided electrical energy from a wall outlet, and cooling is provided by a refrigeration unit. In accordance with another aspect of this invention, apparatus for preventing secondary ischemic injury in a patient with an ischemic condition is provided where evenly distributed jets of cooling fluid is directed at the scalp of the patient using a head-cooling device, and the neck of the patient is cooled using a neck-cooling device, where the means of cooling the head and the neck is provided by a portable console. In accordance with another aspect of this invention, apparatus for preventing secondary ischemic injury in a patient with an ischemic condition is provided where the head of the patient is cooled with a head-cooling device, and the neck of the patient is cooled with a neck-cooling device, where the means of cooling the head and the neck is provided by a portable console. In accordance with another aspect of this invention, apparatus for preventing secondary ischemic injury in a patient with an ischemic condition is provided where the head of the patient is cooled using a head-cooling device, and the neck of the patient is cooled using a neck-cooling device, where the means of cooling the head and the neck is provided by a console where the console is provided electrical energy from a wall outlet, and cooling is provided by a refrigeration unit.

OBJECT AND ADVANTAGES

Accordingly, besides the objects and advantages of the method and apparatus to induce hypothermia to prevent secondary ischemic injury in patients with an ischemic condition described in my patent above, several objects and advantages of the present invention are:

(a) to provide a method of inducing hypothermia in a patient at risk of secondary ischemic injury rapidly;

(b) to provide a method of initiating hypothermia therapy in a patient at risk of secondary ischemic injury prior to arrival at the hospital;

(c) to provide a method of inducing hypothermia in a patient at risk of secondary ischemic injury where protective levels of hypothermia is rapidly and preferentially induced in the brain;

(d) to provide a method of inducing hypothermia in a patient at risk of secondary ischemic injury where protective levels of hypothermia is induced in the brain within 5 to 30 minutes, and where protective levels of hypothermia is induced in the body within 30 to 90 minutes;

(e) to provide a method of rapidly inducing hypothermia in the pre-hospital setting, or upon arrival at the hospital in a patient with cardiac arrest;

(f) to provide a method of rapidly inducing hypothermia in the pre-hospital setting, or upon arrival at the hospital in a patient with acute myocardial infarction;

(g) to provide a method of rapidly inducing hypothermia in the pre-hospital setting, or upon arrival at the hospital in a patient with brain trauma;

(h) to provide a method of rapidly inducing hypothermia in the pre-hospital setting, or upon arrival at the hospital in a patient with stroke;

(i) to provide apparatus for inducing hypothermia in a patient at risk of secondary ischemic injury according to the objectives stated above;

(j) to provide a body cooling system that consists of a head-cooling device, and a console;

(k) to provide a body cooling system that consists of a head-cooling device, a neck cooling device, and a console;

(l) to provide a body cooling system that is non-invasive, and does not require specialized skills to apply;

(m) to provide a body cooling system that is compatible with emergency medical treatment practices;

(n) to provide a portable body cooling system that is capable of providing cooling for 1 to 4 hours using internal batteries;

DRAWING FIGURES

DESCRIPTION—FIG. 1–8

Figure 1:
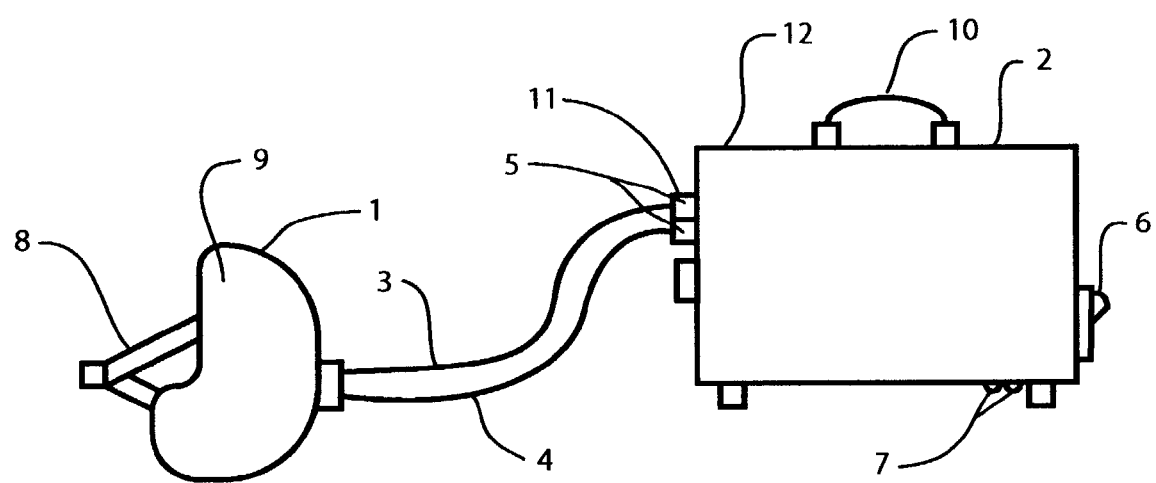
FIG. 1 depicts the body cooling system showing the cooling cap and the console, as well as the umbilical connecting the cooling cap to the console.

FIG. 1 depicts in simple form the body cooling system. Cooling cap 1 is connected to console 2 by an umbilical comprising cooling fluid inlet tube 3, and aspiration tube 4. Cooling cap 1 consists of inner liner (FIG. 3), outer liner 9, chin strap 8, and umbilical comprising cooling fluid inlet tube 3 and aspiration tube 4, and tube fittings 5. Components of the console 1 depicted are the console case 12, carrying handle 10, on/off switch 6, electrical battery recharging contacts 7, and tube fitting receptacles 11. The internal components of the console are described later. The cooling cap 1 is removably connectable to console 2 by tube fittings 5 mounted on the end of cooling fluid inlet tube 3, and aspiration tube 4, and by tube fitting receptacles 11 mounted on console 2. Tube fittings 5 and tube fitting receptacles 11 are readily commercially available. Chinstrap 8 holds cooling cap 1 to the patient's head. Outer liner 9 is an insulating cover made from closed cell foam with a woven outer covering. Chinstrap 8 is bonded to outer liner 8 by thread and adhesive. Console 2 provides cold saline to cooling cap 1 under pressure through cooling fluid inlet tube 3, and removes saline from cooling cap 1 by providing suction to cooling cap 1 through aspiration tube 4. The system is turned on and off by on/off switch 6. An internal electrical battery (not shown) may be recharged by a recharging cradle (not shown) through electrical battery recharging contacts 7. The console is approximately eighteen inches long, twelve inches high and eight inches deep and weighs between 6 and 15 pounds. Carrying handle 10 allows the console to be carried my emergency medical personnel in close proximity to the patient during patient transport.

Figure 2:
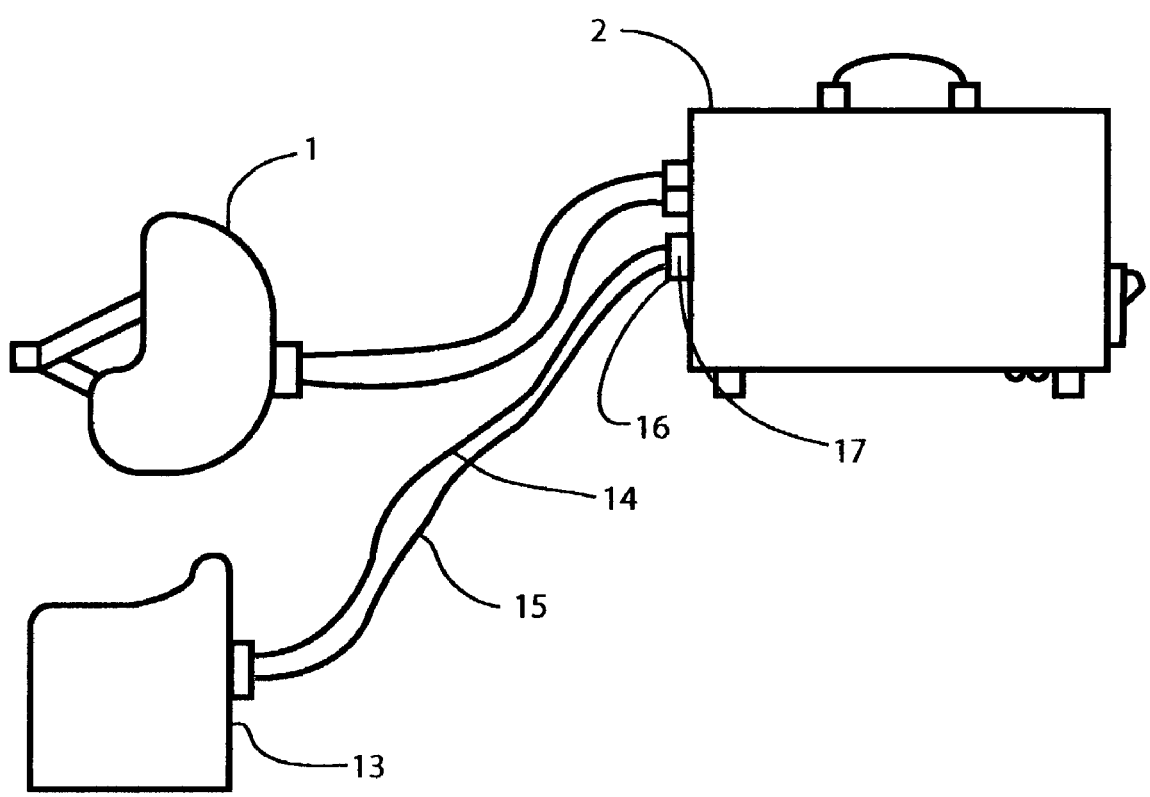
FIG. 2 depicts the body cooling system showing the cooling cap, the cooling collar and console, as well as the umbilical connecting the cooling cap and cooling collar to the console.

FIG. 2 depicts the body cooling system with cooling cap 1 connected to console 2 as depicted in FIG. 1, with cooling collar 13 also connected to console 2 by an umbilical comprising cooling fluid inlet tube 14, and cooling fluid return tube 15. The cooling collar 13 is removably connected to the console 2 by tube fittings 16 mounted on the end of cooling fluid inlet tube 14, and cooling fluid return tube 15, and tube fitting receptacles 17 mounted on console 2. Tube fittings 16 and tube fitting receptacles 17 are readily commercially available. Console 2 provides cold saline to cooling cap 1 as described in FIG. 1, and also provides cold saline to cooling collar 13 under pressure. The cold saline circulates through channels in the wall of cooling collar 13 to cool the neck of the patient (see FIG. 4) and returns to the console through cooling fluid return tube 15.

Figure 3:
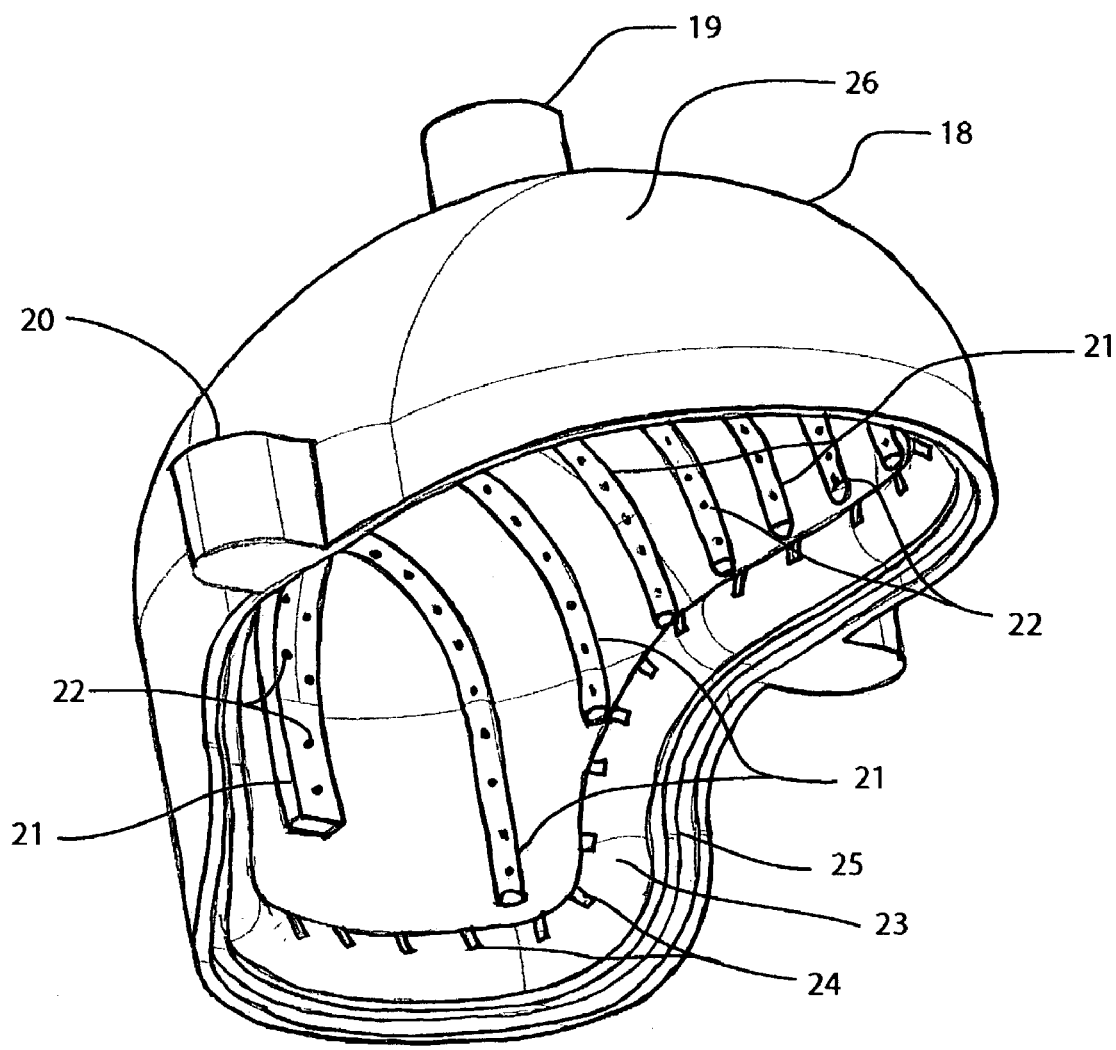
FIG. 3 depicts the inner liner of the cooling cap.

FIG. 3 depicts the inner liner 18 of cooling cap 1 (FIG. 1 & 2). Inner liner 18 consists of inner shell 25, and outer shell 26. Inner shell 25 and outer shell 26 are molded from an elastomer material such as silicone rubber. Inner shell 25, and outer shell 26 are bonded together with adhesive. Channels molded in inner shell 25 form fluid channels 21, and aspiration channel 23 once the inner shell 25, and outer shell 26 are bonded together. Inlet manifold 19 is in fluid communication with fluid channels 21. Aspiration manifold(s) 20 are in fluid communication with aspiration channel 23. Inlet manifold is connected to cooling fluid inlet tube 3 (FIG. 1) with tube fitting (not shown). Aspiration manifold(s) is connected to aspiration tube 4 (FIG. 1) with tube fitting (not shown). Fluid jets 22 are located incrementally along fluid channels 21 as shown. Aspiration ports 24 are located incrementally along aspiration channel 23 as shown. Cold saline enters inner liner 18 through inlet manifold under pressure as provided by console 2, and cooling fluid inlet tube 3 (FIG. 1). The cold saline is distributed through the walls of inner liner 18 by fluid channels 21. The cold saline exits fluid channels 21 through fluid jets 22 which direct the cold saline at the patient's head. Cooling jets 22 are holes through the wall of inner shell 25 and are sized such that the cold saline exits the fluid channel with sufficient velocity that the saline penetrates the patients hair, and reaches the patients scalp. Fluid jets are between 0.010 and 0.040 inches in diameter. The inner liner 18 contains between 25 and 150 fluid jets 22 which provides for even distribution of saline about the patient's head. Cold saline is provided to the inner liner 18 at a pressure of between 5 PSI and 50 PSI by the control console 2 (FIGS. 1 & 2). Suction is applied to aspiration manifold(s) 20 by the console 2 and aspiration tube 4 (FIGS. 1 & 2) which is in fluid communication with aspiration channel 23. Air and saline are drawn into aspiration channel 23 through aspiration ports 24 and is returned to console 2 through aspiration tube 4 (FIG. 1). The combination of suction, and the construction of aspiration channel 23 as shown when placed on a patient's head induces a pressure between the patient's head and inner liner 18 below atmospheric pressure thereby containing the saline under the inner liner 18.

Figure 4A:
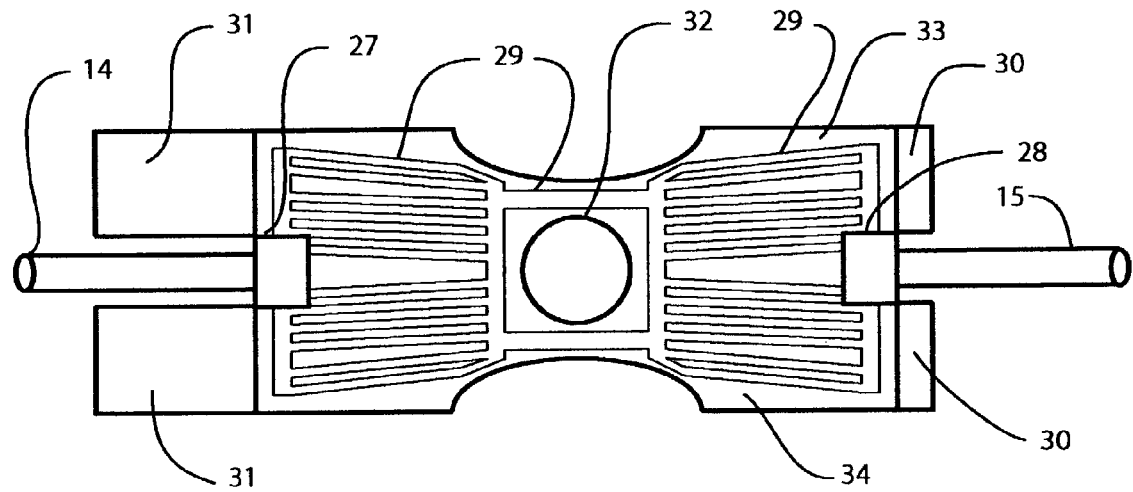
FIG. 4A depicts the front view of the cooling collar.
Figure 4B:
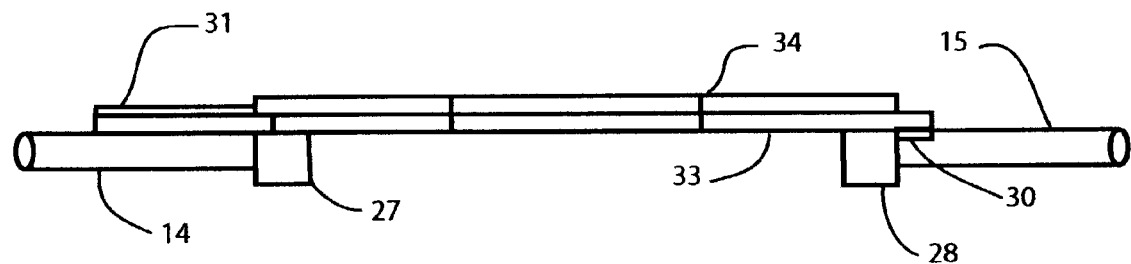
FIG. 4B depicts the side view of the cooling collar.

FIG. 4A depicts a front view of cooling collar 13. Cooling collar 13 consists of cooling fluid inlet tube 14, cooling fluid return tube 15, inlet manifold 27, outlet manifold 28, cooling channels 29 (shown in phantom) formed between inner layer 34 (opposite surface shown), and outer layer 33, Velcro® hook 30 (opposite surface shown), Velcro® loop 31, and tracheotomy hole 32. Cold saline is supplied to cooling collar 13 by console 2 (FIG. 2) under pressure through cooling fluid inlet tube 14. Cold saline enters cooling collar 13 through inlet manifold 27, then flows through multiple cooling channels 29 as shown, and exits cooling collar 13 through outlet manifold 28, and is returned to console 2 (FIG. 2) through cooling fluid return tube 15. Cooling collar 13 is wrapped around the patient's neck in a circular manner and fasted with Velcro hook® 30, and Velcro® loop 31. Tracheotomy hole 32 is positioned over the patient's trachea to provide for emergency tracheotomy. Inner layer 34 is bonded to outer layer 33 by adhesive, or by a thermal bonding method depending on the material selected for the inner layer 34, and outer layer 33. Cooling channels are formed by masking, where there is no bond between inner layer 34, and outer layer 33. Inner layer 34 is formed from a sheet of polymer, or metal foil, or a lamination of polymer and metal foil. Inner layer 34 is between 0.001 and 0.008 inches thick. Outer layer 33 is formed from a sheet of polymer and is between 0.015 and 0.125 inches thick. Inlet manifold 27, and outlet manifold 28 are integrated into the cooling collar 13 during the bonding process (see FIG. 5). Velcro® hook 30, and Velcro® loop are bonded to cooling collar 13 with adhesive and thread. Cooling fluid inlet tube 14, and cooling fluid return tube 15 are made from vinyl tubing or a suitable equivalent and are 0.25 to 0.375 inches in diameter and have a wall thickness of 0.010 to 0.060. Fluid fittings (not shown) mounted on opposite ends of cooling fluid inlet tube 14, and cooling fluid return tube 15 provide removable connection to console 2 (FIG. 2). FIG. 4B depicts a side view of cooling collar 13. Cooling collar 13 is between 4 and 6 inches high, and has a length of between 12 and 20 inches to accommodate the circumference of a variety of patient's necks. The construction of the Velcro® fastening means 30 & 31 as shown provides for proper fit among various patients.

Figure 5:
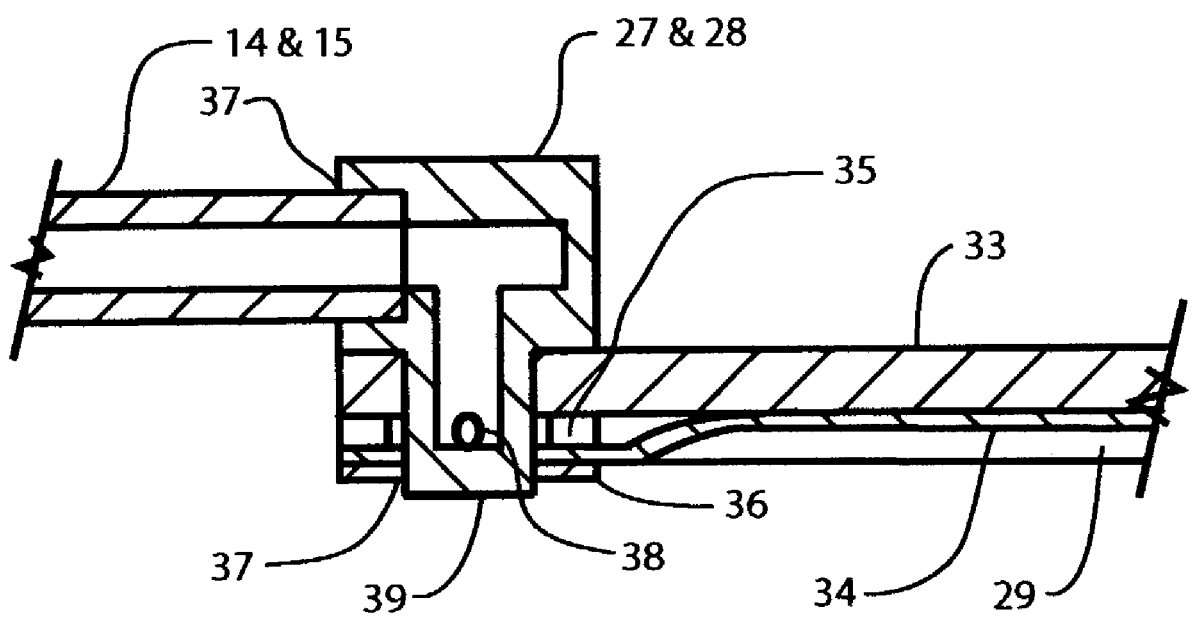
FIG. 5 depicts a sectional view of the construction of the cooling collar.

FIG. 5 depicts in sectional view the attachment of both the inlet manifold 27, and outlet manifold 28 to cooling collar 13. Cooling fluid inlet tube 14 is joined to inlet manifold 27 using adhesive 37, or a barbed tube fitting (not shown). Spacer 35 separates inner layer 34 from outer layer 33 about the circumference of manifold stem 39. Hole 38 is in radial alignment with a hole (not shown) in spacer 35. Inner liner 34 is sandwiched between spacer 35 and washer 36. The assembly is held together with adhesive 37, or is thermally bonded together. Cold saline flows from cooling fluid inlet tube 14 into inlet manifold 27, though hole 38, and through hole (not shown) in space 35 and into fluid channels 29.

Figure 6:
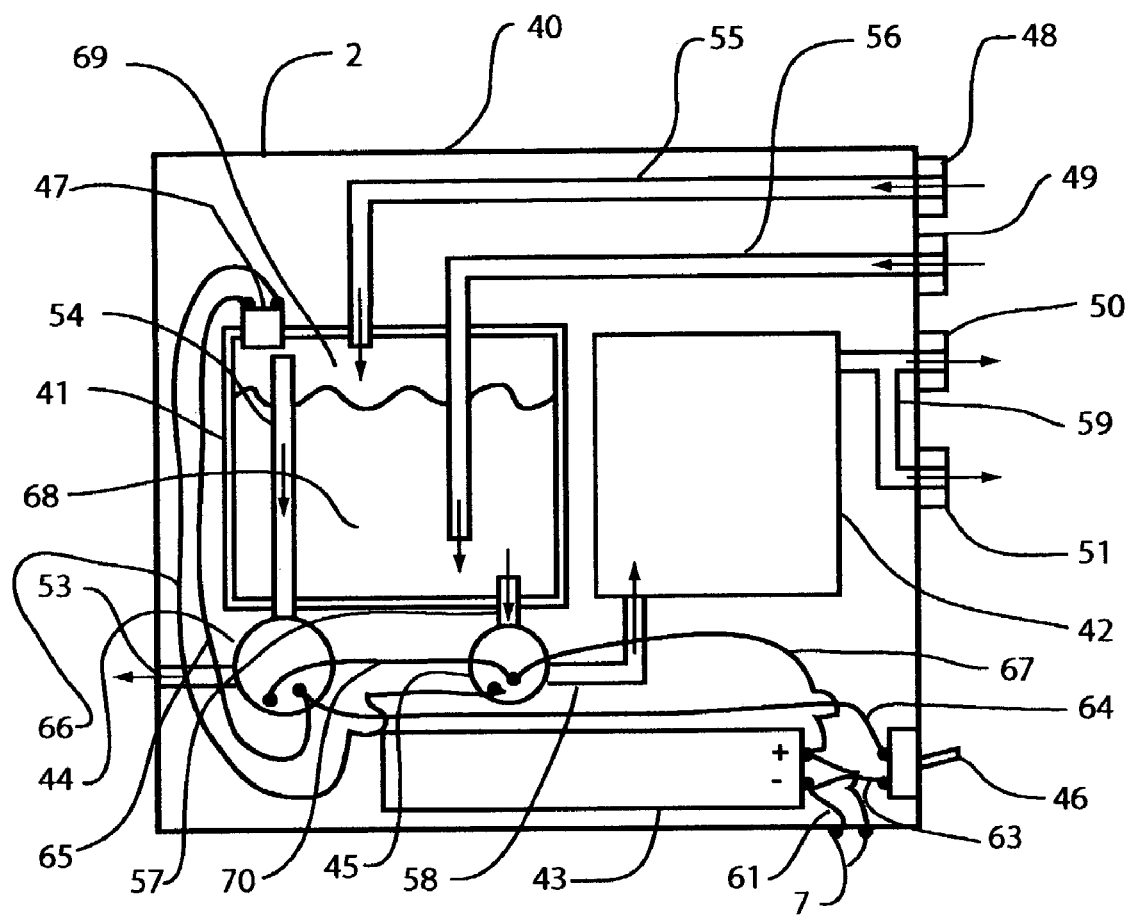
FIG. 6 depicts a schematic of the console.

FIG. 6 depicts console 2 (FIGS. 1 & 2) in schematic form. Console 2 consists of a case 40 which contains the following components: Cooling fluid reservoir 41, thermal battery 42, electrical battery 43, air pump 44, water pump 45, on/off switch 46, pressure switch 47, cooling cap aspiration tube receptacle 48, cooling collar fluid return tube receptacle 49, cooling cap fluid inlet tube receptacle 50, cooling collar fluid inlet tube receptacle 51, air vent 53, vacuum tube 54, aspiration tube 55, fluid tubes 56, 57, 58, 59 and 60, wires 61, 62, 63, 64, 65, 66, and 67, and 69, and electrical contacts 7. Reservoir 41 is air tight and contains saline 68, and air 69. Air pump 44, when activated pumps air 69 from reservoir 41, through vacuum tube 54, out of case 40 trough air vent 53 which creates a pressure within reservoir 41 below atmospheric pressure. Water pump 45 when activated pumps saline 68 from reservoir 41, through thermal battery 42, to cooling cap 1 and cooling collar 13 (FIGS. 1 & 2), and is then returned to reservoir 41 through aspiration tube 55, and fluid tube 56. Thermal battery 42 removes heat from saline 68 as saline 68 traverses through thermal battery 42 thereby lowering the temperature of saline 68. Electrical battery 43 provides electrical power to air pump 44, and water pump 45, and may be recharged by external means through electrical contacts 7 mounted on the external surface of console case 40. Air pump 44 provides a means of aspiration for cooling cap 1 (FIGS. 1 & 2), and water pump 45 provides a means for supplying saline 68 under pressure to cooling cap 1 and cooling collar 13 (FIGS. 1 & 2). Thermal battery 42 provides a means for making saline 68 cold. Cooling cap aspiration tube receptacle 48 is mounted on console case 40, and provides removable connection of cooling cap 1 aspiration tube 4 (FIG. 1) to console 2. Cooling collar fluid return tube receptacle 49 is mounted on console case 40, and provides removable connection of cooling collar 13 cooling fluid return tube 15 (FIG. 2) to console 2. Cooling cap fluid inlet tube receptacle 50 is mounted on console case 40, and provides removable connection of cooling cap 1 cooling fluid inlet tube 3 (FIG. 1) to console 2. Cooling collar fluid inlet tube receptacle 51 is mounted on console case 40, and provides removable connection of cooling collar 13 cooling fluid inlet tube 14 (FIG. 2) to console 2. Receptacles 48, 49, 50 and 51 provide a valve mechanism where when a respective tube is connected to receptacle, fluid communication is provided between the tube and the receptacle, and where if a tube is not connected to the receptacle, a valve within the receptacle closes and prevents fluid communication outside of console 2. Fluid tube 55 provides fluid communication between cooling cap aspiration tube receptacle 48 and reservoir 41 as shown. Fluid tube 56 provides fluid communication between cooling collar fluid return tube receptacle 49 and reservoir 41 as shown. Fluid tube 57 provides fluid communication between reservoir 41 and water pump 45 as shown. Fluid tube 58 provides fluid communication between water pump 45 and thermal battery 42 as shown. Bifurcated fluid tube 59 provides fluid communication between thermal battery 42 and cooling cap fluid inlet tube receptacle 50 and cooling collar fluid inlet tube receptacle 51 as shown. Wire 61 connects the negative terminal of electrical battery 43 to one recharging contact 7.

Wire 62 connects positive terminal of electrical battery 43 to the other recharging contact 7. Wire 63 connects positive terminal of battery 43 to one terminal of on/off switch 46. Wire 64 connects the second terminal of on/off switch 46 to positive terminal of air pump 44. Wire 65 connects positive terminal of air pump 44 to one terminal of pressure switch 47. Wire 66 connects second terminal of pressure switch 47 to positive terminal of water pump 45. Wire 67 connects negative terminal of water pump 45 to negative terminal of battery 43. Wire 70 connects negative terminal of air pump 44 to negative terminal of water pump 45. The body cooling system operates as follows: 1.) Cooling cap 1 and/or cooling collar 13 is fitted to the patient. 2.) Cooling cap 1 and/or cooling collar 13 umbilicals are connected to receptacles 48, 49, 50 and 51. 3.) On/off switch 46 is placed into the "on" position which activates air pump 44. 4.) Pressure switch 47 moves from the normally open position to the closed position and activates water pump 45 once pressure within reservoir 41 is reduced by operation of air pump 44 to a preset pressure of 1 to 10 PSI below atmospheric pressure. If pressure within reservoir 41 rises above preset pressure stated above, pressure switch 47 moves from the closed position to the normally open position and deactivates water pump 45. Note: this mechanism ensures that a sufficient vacuum is established between the patients head, and cooling cap inner liner 18 (FIG. 3) so that when cold saline in introduced into cooling cap inner liner 18 by activation of water pump 45 that the saline will not leak out of the cooling cap inner liner 18, and will be returned to the console by the aspiration mechanism described above. 5.) On/off switch 46 is moved to the off position once hypothermia therapy is concluded. 6.) Cooling cap 1, and/or cooling collar 13 is removed from the patient.

Figure 7:
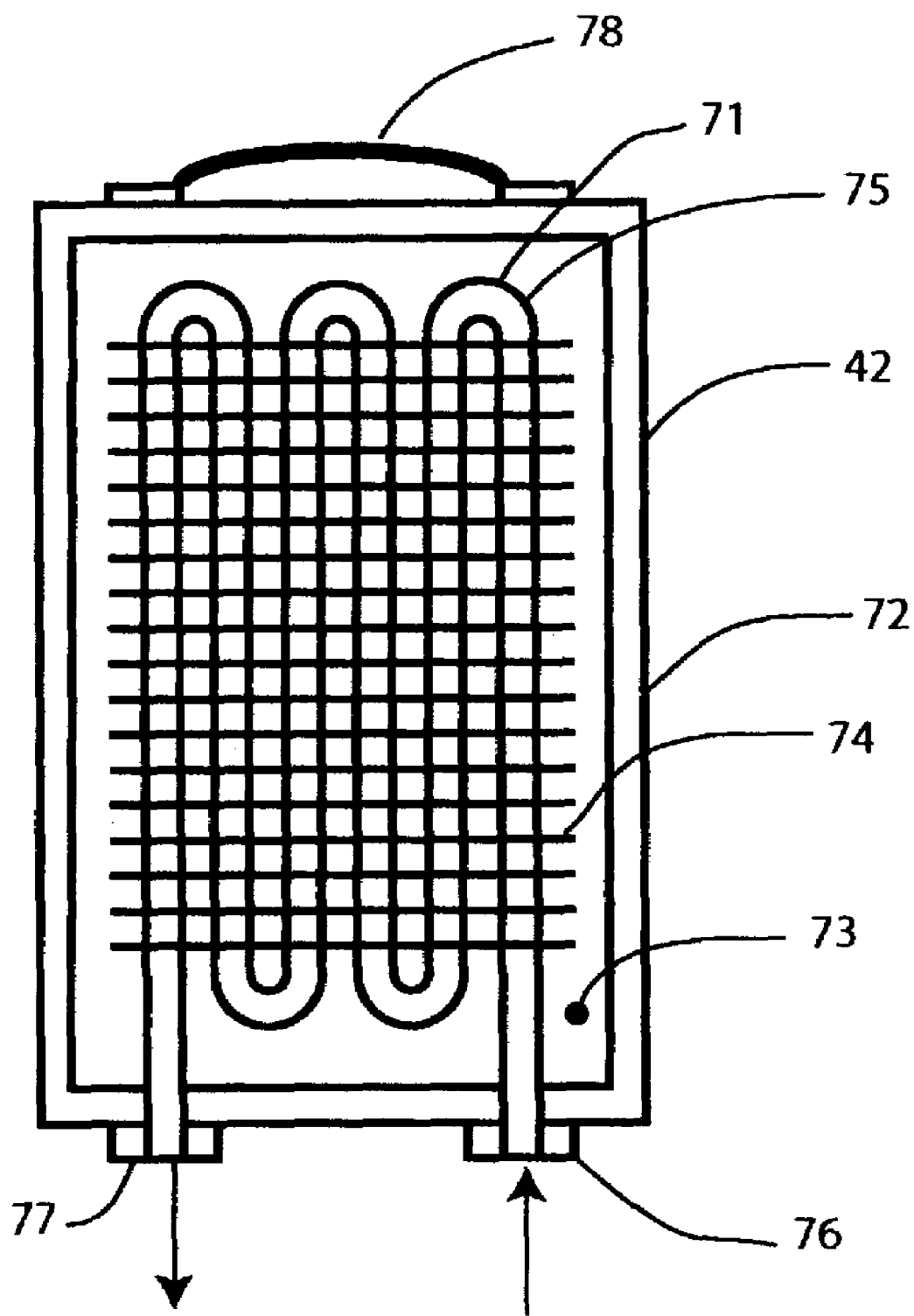
FIG. 7 depicts a sectional view of the thermal battery.

FIG. 7 depicts in schematic form the thermal battery 42. Thermal battery 42 consists of housing 72, heat exchanger 71 consisting of heat exchanger tube 75 and optionally heat exchanger fins 74, fluid inlet fitting 76, fluid outlet fitting 77, cooling medium 73, and handle 78. Housing 72 contains heat exchanger 71 and cooling medium 73 and is molded from a polymer such as high-density polyethylene. Cooling medium 73 is a liquid solution or water, which has the property of freezing and melting at a constant temperature. Heat exchanger 71 consists of a length of heat exchanger tube 75, which provides a fluid path for saline 68 (FIG. 6) internal to housing 72 where heat exchanger tube 75 is surrounded by and in thermal contact with cooling medium 73. Heat exchanger tube 75 may be constructed from stainless steel tubing and has an inner diameter between 0.25 inches and 0.5 inches, and has a wall thickness between 0.005 and 0.020 inches. The shape heat exchanger tube 75 may be serpentine as shown, or some other shape. The straight-line length of heat exchanger tube 75 is between 12 inches and 120 inches. Metal heat exchanger fins 74 may be bonded to heat exchanger tube 75 to enhance heat transfer from cooling medium 73 to saline 68 (FIG. 6) as it passes through heat exchanger tube 75. Housing 72 is constructed so that thermal battery 42 functions as a cassette and may be placed into, and removed from console 2 (FIGS. 1, 2 & 6). Console 2 (FIGS. 1, 2, & 6) is designed to receive thermal battery 42 as a cassette and is configured to provide easy user access to thermal battery 42, and is configured to provide thermal insulation to thermal battery 42 to prevent absorbsion of ambient heat. Fluid inlet fitting 76, and fluid outlet fitting 77 provide fluid connection to console 2 (FIGS. 1, 2, & 6) and mate with receptacles in console 2. Handle 78 facilitates placement and removal of thermal battery 42 from console 2. Thermal battery 42 is charged by placing thermal battery 42 into a freezer for a period of time sufficient to convert cooling medium 73 from a liquid state to a solid state. Cooling medium 73 reverts back to a liquid state during use in patient cooling by absorbing heat from the patients body as transferred to the thermal battery 42 by circulation of saline 68 as previously described. Cooling medium 73 is formulated to freeze and melt at a temperature between −15 and +10 degrees centigrade. Cooling medium 73 may be a solution of salt water, or a solution of water and another substance, or may be water. Thermal battery 42 contains between 1 and 10 pounds of cooling medium 73, and provides for patient cooling for a duration of between 15 and 240 minutes.

Figure 8:
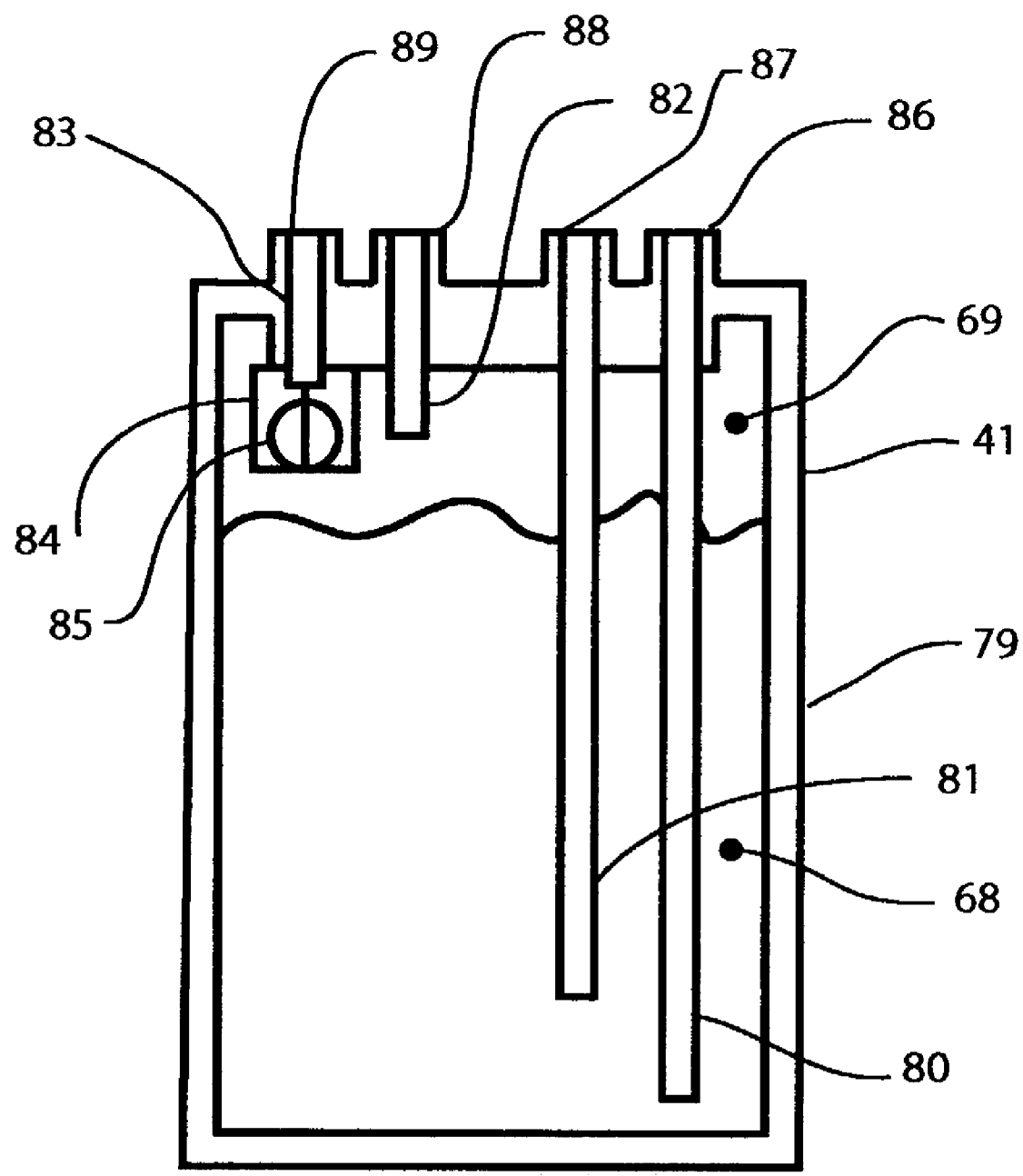
FIG. 8 depicts a sectional view of the fluid reservoir.

FIG. 8 depicts the reservoir 41 in schematic form. Reservoir 41 consists of housing 79 which contains saline 68 and air 69, fluid outlet pipe 80, fluid return pipe 81, aspiration pipe 82, vacuum pipe 83, cage 84, ball 85, fluid outlet pipe fitting 86, fluid return pipe fitting 87, aspiration pipe fitting 88, and vacuum pipe fitting 89. Housing 79 is molded from a suitable polymer such as high-density polyethylene and has a fluid capacity of 1 to 4 liters. Fluid outlet pipe 80 and fluid outlet pipe fitting 86 provides connection to the low-pressure side of water pump 45 (FIG. 6) and is analogous to fluid tube 57 (FIG. 6). Fluid return pipe 81 and fluid return pipe fitting 87 provide connection to cooling collar fluid return tube receptacle 49 (FIG. 6) and is analogous to fluid tube 56 (FIG. 6). Aspiration pipe 82 and aspiration pipe fitting 88 provides connection to cooling cap aspiration tube receptacle 48 (FIG. 6) and is analogous to fluid tube 55 (FIG. 6). Vacuum pipe 83 and vacuum pipe fitting 89 provide connection to the low pressure side of air pump 44 (FIG. 6) and is analogous to vacuum tube 54 (FIG. 6). Ball 84 is buoyant in water and is held in close proximity of the internal end of vacuum pipe 83 by cage 85. Ball 84 and cage 85 function as a valve to prevent any saline from being drawn into vacuum tube 83 in the event the reservoir 41 does not remain upright as shown. Housing 79 is constructed so that reservoir 41 functions as a cassette and may be placed into, and removed from console 2 (FIGS. 1, 2 & 6). Console 2 (FIGS. 1, 2, & 6) is designed to receive reservoir 41 as a cassette and is configured to provide easy user access to reservoir 41 and is configured to provide thermal insulation to reservoir 41 prevent absorbsion of ambient heat. Connection of the reservoir 41 to apparatus contained in console 2 (FIGS. 1,2, & 6) as described above is provided by a receptacle (not shown) that is integral with console 2.

Alternate Embodiments

The thermal battery may be constructed to be non-rechargeable where within the housing are two chambers where each chamber contains a chemical. The thermal battery is manufactured, sold, and stored where the two chemicals are isolated from each other by chamber walls. Prior to use, the chemicals are mixed together to initiate an exothermal reaction where the reactants are in thermal contact with the heat exchanger and the exothermal reaction results in cooling of the saline as it passes through the heat exchanger. A means is provided for the user to quickly and easily initiate the exothermal reaction by providing a mechanism to disrupt the walls of the chambers separating the two chemicals thereby allowing the two chemicals to mix by diffusion.

The body cooling system disclosed above may be configured where a thermal battery, as a separate component is not required for operation, instead, ice may be placed into the reservoir, where the ice in the reservoir provides body cooling.

The cooling collar may incorporate a cooling means similar to the cooling cap where cold saline is directly applied to the neck, and an aspiration system scavenges the saline.

The cooling fluid may be a liquid other than saline.

The cooling collar may be physically constructed to provide both neck cooling, and head immobilization.

The cooling cap, and the cooling collar may be integrated into a single unit, with a single umbilical.

The cooling cap, and cooling collar may be provided in a variety of sizes to accommodate a variety of head sizes and neck sizes, and patient age.

The means of scavenging the saline from the cooling cap may be provided by a means other than aspiration.

The means of applying cold saline directly to the scalp may be provided by a means other than multiple jets.

The console may be configured to be a stationary unit that operates from a wall outlet, and contains a refrigeration unit to provide body cooling.

The body cooling system may include physiological sensors placed on or into the patient to monitor body cooling and control the operation of the consol so as to control body cooling.

The console may have sensors contained within that monitor the operation of the system and control body cooling.

The system may contain interlocks that prevent operation of the system if the user does not operate the system correctly, or the system malfunctions.

The console may contain electronic displays or mechanical indicators that provide the user information on the operation of the system, activation of one or more interlocks, and/or the status of body cooling.

Advantages

From the description above there are a number of advantages my method and apparatus for rapidly inducing hypothermia provides:

(a) The therapeutic agent (hypothermia) for preventing secondary ischemic injury according to this invention is rapidly applied.

(b) The therapeutic agent (hypothermia) for preventing secondary ischemic injury according to this invention may be applied in the pre-hospital setting.

(c) The method and apparatus for rapidly inducing hypothermia according to this invention provides for preferential brain cooling.

(d) The therapeutic agent (hypothermia) for preventing secondary ischemic injury according to this invention may be applied by emergency medical personnel without surgical skill.

(e) The method for and apparatus for rapidly inducing hypothermia provides for a reduction of death and disability from ischemia.

I claim:

1. A portable system for inducing hypothermia as a therapeutic agent in a patient in the pre-hospital setting, or in the emergency room of a hospital comprising:
   (a) a small battery operated console, comprising a fluid reservoir, a thermal battery, an electrical battery, a water pump, an air pump, and control circuitry, and
   (b) a cooling cap comprising a fluid distribution means for infusing the scalp of said patient with cold fluid, and an aspiration manifold disposed circumferentially about the internal rim of said cooling cap, and
   (c) an umbilical providing at least two fluid passages between said control console and said cooling cap,
whereby said console provides cold fluid to said cooling cap under positive gage pressure by means provided by said water pump, where said cold fluid is scavenged from said aspiration manifold under negative gage pressure by means provided by said air pump, and wherein said system provides a means to cool a second part of said patient's body with a second body-cooling garment.

2. The system of claim 1 wherein said system is controlled by said control circuitry according to information provided by a physiological sensor placed on or into the body of said patient.

3. The system in claim 1 wherein said fluid reservoir and said thermal battery comprise a container containing ice and fluid.

4. The system in claim 1 wherein said fluid is water.

5. The system in claim 1 wherein said fluid is saline.

6. The system in claim 1 wherein said thermal battery does not alter the chemical properties of said fluid as heat is absorbed by said thermal battery.

7. The system of claim 1 wherein the size of said console allows said console to be carried by hand by emergency medical personnel to the scene of an emergency, and to be utilized at said scene.

8. The system of claim 1 wherein the weight of said console in between approximately 6 and 15 pounds.

9. The system of claim 1 wherein said electrical battery and said thermal battery each have a capacity to provide operation of said system for a period of time greater than one hour.

10. The system of claim 1 wherein said fluid reservoir, and/or said thermal battery may be constructed as an insert able cassette, and said console may be constructed to receive at least one said insert able cassette.

11. The system of claim 1 wherein said cooling cap is constructed such that said cooling is substantially limited to the surface of the head in the vicinity of the cranium.

12. The system of claim 1 wherein said fluid is supplied under positive gage pressure to said cooling cap at a temperature near zero degrees centigrade.

13. A method for preventing death and morbidity in a patient found with a life threatening ischemic condition comprising the steps of:
   (a) bringing a hypothermia induction system comprising a portable console, a head-cooling cap, and an umbilical, to the location said patient was found, then
   (b) placing said head-cooling cap onto the head of said patient, then
   (c) activating said hypothermia induction system prior to or as said patient is transported to a hospital,
whereby, said hypothermia induction system comprises a means to infuse the scalp of said patient with cold fluid, a means to scavenge said fluid, and a means to operate said system on internal batteries for a period of time greater than one hour.

14. The method of claim 13 wherein said life threatening ischemic condition is cardiac arrest.

15. The method of claim 13 wherein said life threatening ischemic condition is myocardial infarction.

16. The method of claim 13 wherein said life threatening ischemic condition is ischemic stroke.

17. The method of claim 13 wherein said life threatening ischemic condition is hypovolemia secondary to hemorrhage.

18. The method of claim 13 wherein said life threatening ischemic condition is head trauma.

19. The method of claim 13 wherein said life threatening ischemic condition is intracranial hemorrhage.

20. The method of claim 13 wherein said hypothermia induction system provides surgical access to the neck, arms, chest, torso and groin of said patient during use.

21. A cooling device comprising:
a cap having an outer surface and an inner surface and the cap defining an edge, wherein the cap comprises an outer liner formed of an insulation material coupled to the outer surface of the cap;
an inlet in communication with the cap, the inlet configured to distribute cooling fluid, under pressure from a pressure source, to a head; and
an aspiration channel disposed on the inner surface of the cap about the edge defined by the cap, the aspiration channel configured to fluidly communicate with a suction source to remove air and cooling fluid from the head and to seal the edge of the cap to the head.

22. The cooling device of claim 21 wherein the inner surface of the cap defines a fluid channel in fluid communication with the inlet, the fluid channel having a plurality of fluid jets.

23. The cooling device of claim 21 wherein the inner surface of the cap defines a head-shape configured to substantially mirror at least a portion of a shape of the head.

24. The cooling device of claim 21 wherein the cooling device comprises a cooling collar integrally formed with the cap, the cooling collar configured to provide cooling to a neck of the head.

25. The cooling device of claim 21 wherein the aspiration channel defines a plurality of aspiration ports configured to direct air and cooling fluid from the head to the aspiration channel.

26. The cooling device of claim 21 wherein the cooling device is configured to induce localized hypothermia within a patient.

27. A cooling system comprising:
a console having:
a fluid reservoir configured to hold a cooling fluid and comprising a pressure switch configured to engage a closed position to activate the pressure source when a pressure within the fluid reservoir is below atmospheric pressure;
a pressure source in fluid communication with the fluid reservoir; and a suction source in fluid communication with the fluid reservoir; and
a cooling device having:
a cap having an outer surface and an inner surface and the cap defining an edge, an inlet defined by the cap, the inlet configured to distribute cooling fluid, under pressure from the pressure source, to a head, and
an aspiration channel disposed on the inner surface of the cap about the edge defined by the cap, the aspiration channel configured to fluidly communicate with a suction source to remove air and cooling fluid from the head and to seal the edge of the cap to the head.

28. The cooling system of claim 27 wherein the inner surface of the cap defines a fluid channel in fluid communication with the inlet manifold having a plurality of fluid jets.

29. The cooling system of claim 27 wherein the console comprises a thermal battery in fluid communication with the fluid reservoir, the thermal battery configured to reduce the temperature of the cooling fluid held by the reservoir.

30. The cooling system of claim 27 further comprising a cooling collar in fluid communication with the fluid reservoir, the cooling collar configured to provide cooling to a neck of the head.

31. The cooling system of claim 27 further comprising a physiological sensor coupled to the console, the physiological sensor configured to monitor body cooling and control operation of the console to control body cooling.

32. A method for inducing hypothermia in a patient comprising:
placing a cooling device on a head of a patient, the cooling device having a cap having an outer surface and an inner surface and the cap defining an edge, an inlet in communication with the cap, the inlet configured to distribute cooling fluid, under pressure from a pressure source, to a head, and an aspiration channel disposed on the inner surface of the cap about the edge defined by the cap, the aspiration channel configured to fluidly communicate with a suction source to remove air and cooling fluid from the head and to seal the edge of the cap to the head;
coupling the inlet to the pressure source;
coupling the aspiration channel to the suction source; and
engaging the pressure source and the suction source to, respectively, provide fluid under pressure to the inlet of the cooling device and remove air and cooling fluid from the head to seal the edge of the cap to the head.

33. The method of claim 32 further comprising:
placing a physiological sensor in electrical communication with a console, the console having the pressure source and the aspiration source; and
placing the physiological sensor in communication with the patient, the physiological sensor configured to monitor body cooling and control operation of the pressure source and suction source of the console to control body cooling.

34. A portable system for inducing hypothermia as a therapeutic agent in a patient in the pre-hospital setting, or in the emergency room of a hospital comprising:
(a) a small battery operated console, comprising a fluid reservoir, a thermal battery, an electrical battery, a water pump, an air pump, and control circuitry, and
(b) a cooling cap comprising a fluid distribution means for infusing the scalp of said patient with cold fluid, and an aspiration manifold disposed circumferentially about the internal rim of said cooling cap, and
(c) an umbilical providing at least two fluid passages between said control console and said cooling cap, whereby said console provides cold fluid to said cooling cap under positive gage pressure by means provided by said water pump, and where said cold fluid is scavenged from said aspiration manifold under negative gage pressure by means provided by said air pump, wherein said system is controlled by said control circuitry according to information provided by a physiological sensor placed on or into the body of said patient.

35. A portable system for inducing hypothermia as a therapeutic agent in a patient in the pre-hospital setting, or in the emergency room of a hospital comprising:
(a) a small battery operated console, comprising a fluid reservoir, a thermal battery, an electrical battery, a water pump, an air pump, and control circuitry, and
(b) a cooling cap comprising a fluid distribution means for infusing the scalp of said patient with cold fluid, and an aspiration manifold disposed circumferentially about the internal rim of said cooling cap, and (c) an umbilical providing at least two fluid passages between said control console and said cooling cap, whereby said console provides cold fluid to said cooling cap under positive gage pressure by means provided by said water pump, where said cold fluid is scavenged from said aspiration manifold under negative gage pressure by means provided by said air pump, and wherein the weight of said console is between approximately 6 and 15 pounds.

36. A portable system for inducing hypothermia as a therapeutic agent in a patient in the pre-hospital setting, or in the emergency room of a hospital comprising:
   (a) a small battery operated console, comprising a fluid reservoir, a thermal battery, an electrical battery, a water pump, an air pump, and control circuitry, and
   (b) a cooling cap comprising a fluid distribution means for infusing the scalp of said patient with cold fluid, and an aspiration manifold disposed circumferentially about the internal rim of said cooling cap, and
   (c) an umbilical providing at least two fluid passages between said control console and said cooling cap, whereby said console provides cold fluid to said cooling cap under positive gage pressure by means provided by said water pump, where said cold fluid is scavenged from said aspiration manifold under negative gage pressure by means provided by said air pump, and wherein said electrical battery and said thermal battery each have a capacity to provide operation of said system for a period of time greater than one hour.

37. A portable system for inducing hypothermia as a therapeutic agent in a patient in the pre-hospital setting, or in the emergency room of a hospital comprising:
   (a) a small battery operated console, comprising a fluid reservoir, a thermal battery, an electrical battery, a water pump, an air pump, and control circuitry, and
   (b) a cooling cap comprising a fluid distribution means for infusing the scalp of said patient with cold fluid, and an aspiration manifold disposed circumferentially about the internal rim of said cooling cap, and
   (c) an umbilical providing at least two fluid passages between said control console and said cooling cap, whereby said console provides cold fluid to said cooling cap under positive gage pressure by means provided by said water pump, where said cold fluid is scavenged from said aspiration manifold under negative gage pressure by means provided by said air pump and wherein said fluid reservoir, and/or said thermal battery may be constructed as an insertable cassette, and said console may be constructed to receive at least one said insert able cassette.

38. A cooling device comprising:
   a cap having an outer surface and an inner surface and the cap defining an edge;
   an inlet in communication with the cap, the inlet configured to distribute cooling fluid, under pressure from a pressure source, to a head;
   an aspiration channel disposed on the inner surface of the cap about the edge defined by the cap, the aspiration channel configured to fluidly communicate with a suction source to remove air and cooling fluid from the head and to seal the edge of the cap to the head; and
   a cooling collar integrally formed with the cap, the cooling collar configured to provide cooling to a neck of the head.

39. A cooling system comprising:
   a console having:
      a fluid reservoir configured to hold a cooling fluid;
      a pressure source in fluid communication with the fluid reservoir; and a suction source in fluid communication with the fluid reservoir;
   a cooling device having:
      a cap having an outer surface and an inner surface and the cap defining an edge,
      an inlet defined by the cap, the inlet configured to distribute cooling fluid, under pressure from the pressure source, to a head, and
      an aspiration channel disposed on the inner surface of the cap about the edge defined by the cap, the aspiration channel configured to fluidly communicate with a suction source to remove air and cooling fluid from the head and to seal the edge of the cap to the head; and
   a cooling collar in fluid communication with the fluid reservoir, the cooling collar configured to provide cooling to a neck of the head.

* * * * *

UNITED STATES PATENT AND TRADEMARK OFFICE
CERTIFICATE OF CORRECTION

PATENT NO. : 7,008,445 B2  Page 1 of 1
DATED : March 7, 2006
INVENTOR(S) : Charles D. Lennox It is certified that error appears in the above-identified patent and that said Letters Patent is hereby corrected as shown below:

<u>Column 1,</u>
Line 57, change "modem" to -- modern. --.

<u>Column 12,</u>
Line 29, change "in" to -- is --.
Lines 35-36 and 37, change "insert able" to -- insertable. --.

Signed and Sealed this

Sixth Day of June, 2006

JON W. DUDAS
*Director of the United States Patent and Trademark Office*